United States Patent [19]

Mazarin

[11] Patent Number: 4,575,457

[45] Date of Patent: Mar. 11, 1986

[54] PERIODONTAL TOOTHPASTE WITH WOUND-HEALING PROPERTIES

[75] Inventor: Sanford S. Mazarin, Stamford, Conn.

[73] Assignee: American Home Products Corporation, New York, N.Y.

[21] Appl. No.: 613,999

[22] Filed: May 24, 1984

[51] Int. Cl.⁴ .......................... A61K 7/16; A61K 7/18
[52] U.S. Cl. ........................................ 424/52; 424/49; 424/95
[58] Field of Search .................................. 424/49-58, 424/95

[56] References Cited

U.S. PATENT DOCUMENTS

| | | | |
|---|---|---|---|
| 2,239,345 | 4/1941 | Sperti | 424/95 |
| 2,320,478 | 6/1943 | Sperti | 424/95 |
| 2,320,479 | 6/1943 | Sperti | 424/95 |
| 2,789,731 | 4/1957 | Marrafino | 222/94 |
| 4,098,435 | 7/1978 | Weyn | 222/94 |

OTHER PUBLICATIONS

Cerra, M., et al., J. Periodontol. 53:599–603, Oct. 1982.
Stoller, N., et al., presented at the A.A.P. annual session, Research Forum, 1982.
Greenwell, H., et al., J.A.D.A. 106:457–461, Apr., 1983.
Wolff, L., et al., J. Dent. Res. 17:537–540, Sep., 1982.
West, T., et al., J. Periodontol. 54:339–346, Jun. 1983.

*Primary Examiner*—Shep K. Rose
*Attorney, Agent, or Firm*—Walter Patton

[57] ABSTRACT

Pharmaceutical composition of skin respiratory factor (SRF), sodium chloride, bicarbonate, fluoride and zinc chloride in a suitable toothpaste vehicle provides effective therapy for gingivitis when brushed on the teeth and gingivae.

Pharmaceutical composition of SRF in a viscous composition suitable for application to the gingivae and effective over an extended period of time for healing tissue damaged by gingivitis. A toothpaste tube for packaging a pharmaceutical composition of SRF, sodium chloride, bicarbonate, fluoride and zinc chloride.

4 Claims, No Drawings

PERIODONTAL TOOTHPASTE WITH WOUND-HEALING PROPERTIES

TECHNICAL FIELD

Normal gingivae are pink and firmly attached to the underlying alveolar bone. At the enamel-gingival junction, the gingiva forms an epithelial-lined ridge around the teeth. The area between the enamel and the gingivae is called the gingival crevice. Gingivitis develops when large masses of bacteria clog the gingival crevice.

Bacteria invade the surrounding area and form a sticky matrix, called plaque. If plaque is left undisturbed, it calcifies into calculus. Bacteria in plaque produce metabolic by-products, enzymes and toxins. These products diffuse into the immediate surrounding area, irritate the gingivae, and, as a consequence, they trigger a localized inflammatory reaction. The gingivae swell, become reddened and extrude crevicular fluid. Depending on the severity of the condition, the gingivae become sensitive to touch and may spontaneously bleed. As gingivitis advances to periodontitis, the supporting collagen fibers and the alveolar bone begin to degenerate. As a result, teeth become mobile and eventually fall out.

BACKGROUND ART

There are numerous studies that demonstrate that the accumulated plaque at the enamel-gingival junction significantly increases the severity of the gingival disease, while other studies show that when plaque is removed, healthy condition is reestablished. Because of the apparent direct cause and effect relationship between plaque and gingival inflammation, it is widely believed that plaque accumulation is detrimental to gingival health.

It has been suggested that if the accumulation of plaque at the enamel-gingival junction can be prevented or at least retarded, the severity of gingivitis and periodontitis can thereby be reduced.

A widely studied and much discussed method for maintaining periodontal health or even eliminating periodontal disease is simply using sodium chloride, sodium bicarbonate and hydrogen peroxide as a dentifrice in a thorough oral hygiene program. Five scientific studies have evaluated using sodium bicarbonate and hydrogen peroxide as a dentifrice.

These five studies done independently at five different universities totaling 114 patients all showed similar results when evaluating the dentifrices. Sodium bicarbonate and hydrogen peroxide appears to be an adequate dentifrice but is no better than commercially available dentifrices, whether fluoridated, non-fluoridated or powdered.

Cerra, M., et al., J. Periodontol. 53:599–603, October 1982.

Stoller, N., et al., Presented at the A.A.P. annual session, Research Forum, 1982.

Greenwell, H., et al., J.A.D.A. 106:457–461, April, 1983.

Wolff, L., et al., J. Dent. Res. 17:537–540, September, 1982.

West, T., et al., J. Periodontol. 54:339–346, June 1983.

DISCLOSURE OF INVENTION

It has now been discovered that the rate of healing of gingivitis, as characterized by inflammation, bleeding and swelling, can be substantially increased by the daily application to the gingivae of a pharmaceutical composition comprising skin respiratory factor (SRF), sodium chloride and bicarbonate, fluoride and zinc ions in a suitable toothpaste vehicle.

SRF is a commercial material produced by the method set forth in U.S. Pat. Nos. 2,239,345, 2,320,478 and 2,320,479, which are herein incorporated by reference, and is standardized as units with 1 unit (U) of SRF increasing the uptake of oxygen by minced rat abdominal skin (1 mg dry weight) by 1% in a 1-hr. measurement by Warburg manometry.

As an adjunct to the above treatment, a gelatinous adhesive preparation for example with gelatin, carboxymethylcellulose, silica, containing SRF is provided for application to the gingivae. This adhesive preparation can be applied for entended periods and, for example, can provide overnight contact of SRF with the gingivae.

Prolonged contact of the SRF with the basic pH, about 8, of the tooth paste vehicle results in some discoloration (darkening) of the SRF. Accordingly, the present invention provides for packaging the pharmaceutical composition in a toothpaste tube wherein the interfacial contact between the SRF and the remaining components of the toothpaste are minimized. Such toothpaste tubes are described in U.S. Pat. Nos. 2,789,731 and 4,098,435. FIG. 1 of the accompanying drawing illustrates the concept of the tube and will be subsequently described in detail.

DETAILED DESCRIPTION OF INVENTION

The active components of the present pharmaceutical composition are present in the toothpaste vehicle in the following ranges of quantities:

Total fluoride: 900–1100 ppm F-
Soluble fluoride: 1000 ppm F-
SRF: 2700–3300 units/oz.
Bicarbonate ion: 13.05–15.95% w/w
Sodium Chloride: 4.50–10.5% w/w
Zinc ion: 0.108–0.132% w/w In the pharmaceutical compositions of the invention, the bicarbonate, fluoride, and zinc salts that can be used to provide the bicarbonate, fluoride and zinc ions are the pharmaceutically acceptable salts which are compatible with the ingredients of the toothpaste vehicle.

In the pharmaceutical composition of this invention, the zinc salts that could be used to supply all or part of the zinc ion, are the chloride, citrate, acetate, lactate, salicylate, and, in general, glycerol soluble, pharmaceutically acceptable zinc salts. The preferred salt is zinc chloride.

In the pharmaceutical compositions of this invention, the bicarbonates that could be used to supply all or part of the bicarbonate ion are sodium bicarbonate and potassium bicarbonate. The preferred salt is sodium bicarbonate.

In the pharmaceutical composition of this invention, the fluoride salts that could be used to supply all or part of the fluoride ion are pharmaceutically acceptable fluorides such as sodium fluoride, and the like.

The active components are incorporated into a suitable toothpaste vehicle containing polishing agents, thickening agents, sudsing agents, humectants, flavoring agents, and sweetening agents. These agents are standard pharmaceutical tools used in these preparations and are not an essential aspect of this invention.

Therefore, the amount of these additive materials used can be varied.

Any suitable water insoluble polishing agent can be employed in the compositions of this invention, such as, for example, dicalcium phosphate, aluminum hydroxide, calcium carbonate, calcium polymetaphosphate, dicalcium orthophosphate dihydrate, sodium polymetaphosphate and mixtures thereof.

If a thickening agent is required, cellulose derivatives such as, for example, sodium carboxumethylcellulose and sodium carboxymethylhydroxyethyl cellulose or natural gums such as gum arabic or gum tragacanth may be employed.

Exemplary of sudsing agents which may be employed are, for example, sodium lauryl sulfate, sodium N-lauroyl sarcosinate, sulfonated monoglycerides of fatty acids having from 10 to 18 carbon atoms such as, for example, sodium monoglyceride sulfonates or mixtures thereof.

Among the specific compounds which may be employed as humectants are sorbitol, glycerine, polyhydric alcohols of like nature or mixtures thereof.

As examples of compounds that may be used as flavoring agents are clove oil, menthol, peppermint oil, spearmint oil, wintergreen oil, sassafras oil and anise oil. Sweetening agents would include compounds such as, for example, saccharin, dextrose, and sodium cyclamate.

The following examples together with the accompanying drawing further serve to illustrate the pharmaceutical toothpaste compositions of this invention.

EXAMPLE 1

A pharmaceutical toothpaste composition suitable for treatment of gingivitis is formulated from the following ingredients in two separate portions, including a flavor portion, which are then admixed to form the final composition.

| Phase | First Portion Ingredient | % By Weight |
|---|---|---|
| A | Glycerine 96% | 5.00 |
| A | Carboxymethylcellulose 7MF | 1.00 |
| B | Sorbitol 70% | 15.00 |
| C | Deionized Water | 23.05 |
| C | Zinc Chloride | 0.25 |
| C | Sodium Benzoate | 0.10 |
| C | Sodium Saccharine | 0.25 |
| C | Sodium Fluoride | 0.22 |
| C | Sodium Chloride | 5.00 |
| C | SRF | 1.23 |
| C | Sodium Bicarbonate | 20.00 |
| D | Syloid B-30 | 13.00 |
| D | Sicosil 63M | 4.00 |
| E | Titanium Dioxide #3328 | 1.00 |
| E | Sorbitol 70% | 2.00 |
| F | Sorbitol 70% | 5.00 |
| F | Sodium Lauryl Sulfate | 2.40 |
| F | Flavor | 1.50 |

Flavor Portion

The flavor portion which is a component of Phase F above is composed of the following ingredients which are weighed and placed into a suitable stainless steel container fitted with a mixer. The mixer is then started and the mixing is continued until all of the menthol crystals have dissolved.

| Ingredient | % By Weight |
|---|---|
| Cinamic Aldehyde | 8.20 |
| Menthol, Racemic Crystals | 49.30 |
| Methyl Salycilate | 20.50 |
| Peppermint Oil | 4.10 |
| Spearmint Oil | 4.10 |
| Clove Oil | 13.80 |

The toothpaste is produced according to the following procedure:
1. In an appropriate vessel equipped with adequate mixers weigh in glycerine.
2. Blend carboxymethylcellulose with glycerine.
3. Add sorbitol to Phase A.
4. In another vessel, dissolve ingredients of Phase C in order in deionized water. Maintain heat at 50° to 70° C. for a few minutes. Cool to room temperature. Add to first vessel.
5. To a kettle with vacuum draw at least 28 inches of vacuum. Mix under vacuum for 5 minutes.
6. Break vacuum and add dry powders of Phase D to batch one at a time under agitation.
7. Draw vacuum again. Mix under vacuum for 25–30 minutes.
8. Break vacuum. In a separate vessel, disperse titanium dioxide in sorbitol. Add to batch under agitation.
9. Dissolve sodium lauryl sulfate, flavor, and color in sorbitol (Phase F). Add to batch.
10. Reseal and mix under vacuum for 5 minutes.
11. Transfer to storage.

EXAMPLE 2

This embodiment of the pharmaceutical composition of the invention will be described with respect to a toothpaste tube or package in which the SRF is separated from the other active ingredients until the time of use.

FIG. 1 is a vertical central sectional elevation of a dispensing end of a tube useful in packaging the pharmaceutical composition of the present invention. Referring to FIG 1, collapsible dispensing tube 11 has a side wall 13 lined on the inside surface and a shoulder portion 15 terminating in a neck 17 onto which is pressed and held firmly in place a blending fitting 19, preferably made of synthetic organic polymeric plastic materials, such as nylon or other suitable moldable and form-retaining polymer, preferably of the thermoplastic type. Blending fitting 19 includes a longitudinally extending tubular portion 21, the wall 22 of which is shown tapered and containing internal ribs 23. Wall 22 determines a longitudinal passageway 25. A plurality (usually from 2 to 6 but even single passageways may be employed) of transverse passageways 27, located near the joinder of the shoulder and neck portions of the tube, passes through wall 22. The blending fitting includes an externally threaded outer portion 29 and a dispensing opening 31, which is a continuation of passageway 25. A sealing cap 33 may be screwed onto threaded portion 29 of the blending fitting to prevent unintentional discharge of contents from tube 11.

As is illustrated in FIG. 1, initially a first portion of SRF in a suitable vehicle at a pH of about 5 designated 35 is filled into the tube, as is fully described in U.S. Pat. No. 4,098,435, to the level or interface indicated by numeral 37. Preferably then, an "insulating" or protective intermediate layer of non-reactive material 39 is applied and then the second portion of the dentifrice, identified by numeral 41, containing the balance of the periodontal toothpaste ingredients set forth in Example 2 is filled into the tube while the tube is maintained in inverted position, as illustrated. Upon application of pressure to the tube, streams of the first portion of the dentifrice containing SRF pass through openings 27 into passageway 25, forming stripes or "inlays" in the surface of the second portion of the dentifrice in such passageway. Entry of the first portion into the second portion is facilitated by the presence of the "upstream" ribs 23 and a correct and uniform proportion of first dentifrice portion to second dentifrice portion is obtained. Because of the location of the tranverse openings 27, essentially all of the product can be discharged and the dispensed product is of substantially uniform composition throughout dispensing. Ideally, the portion of dispensing passage 31 "downstream" (upon dispensing) of transverse openings 27 will be as short as is feasible so as to minimize contacting of any reactive portions of the dentifrice with each other during storage for any appreciable time between uses.

The material of construction of the tube is preferably a conventional polymeric plastic with polymeric plastic cap and blending fitting. The dentifrice and the different portions thereof, the various compositions of which will be described later, will normally be extrudable through the dispensing opening.

The number of openings through the dispensing passageway walls will be chosen to regulate the desired proportions of the dentifrices to be discharged.

The formulation of the toothpaste of Example 2 is as set forth below.

| Phase | Ingredient | % By Weight |
|---|---|---|
| A | Glycerine 96% | 5.00 |
| A | CMC 7MF | 1.00 |
| B | Sorbitol 70% | 15.00 |
| C | Deionized Water | 24.28 |
| C | Zinc Chloride | 0.25 |
| C | Sodium Benzoate | 0.10 |
| C | Sodium Saccharine | 0.25 |
| C | Sodium Fluoride | 0.22 |
| C | Sodium Chloride | 5.00 |
| C | Sodium Bicarbonate | 20.00 |
| D | Syloid B-30 | 13.00 |
| D | Sicosil 63M | 4.00 |
| E | Titanium Dioxide #3328 | 1.00 |
| E | Sorbitol 70% | 2.00 |
| F | Sorbitol 70% | 5.00 |
| F | Sodium Lauryl Sulfate | 2.40 |
| F | Flavor | 1.50 |
|  | SRF Concentrate Crude | * |

*Adjust concentration of SRF to 3000 units/ounce of product.

The flavor component present to the extent of 1.50% by weight contains the ingredients and is produced by the procedure of Example 1.

The preparation of the first portion of the toothpaste containing the SRF is as follows:

Mix the SRF with one-third of the Sorbitol 70% set forth above for Phase B and one-fifth of the Glycerine 96% set forth above for Phase B. This first portion at a pH of about 5, is first added to the tube of Example 1 and designated 35.

A small amount of Sorbitol 70%, i.e. one-fifth of the amount set forth above for Phase F, is added to the tube to separate the SRF first portion from the higher pH second portion.

The second portion containing the balance of the ingredients is prepared using the procedure described in Example 1 and then added to the tube and sealed.

EXAMPLE 3

The preparation of another embodiment of the periodontal toothpaste of the invention is described below using the following ingredients.

| Ingredient | % w/w Q.S. adjust to |
|---|---|
| Part I | |
| Purified Water Deionized | 100.000 |
| Sodium Benzoate, NF (preservative) | 0.100 |
| Sodium Saccharin, USP | 0.250 |
| Sodium Fluoride, USP | 0.220 |
| Sodium Chloride, USP | 10.000 |
| Zinc Chloride Granular, USP | 0.250 |
| SRF Concentrate Crude | * |
| Sorbitol Solution, USP | 22.000 |
| Sodium Bicarbonate, USP | 15.000 |
| Part II | |
| Glycerin 99 Percent, USP | 3.000 |
| CMC 7MF | 1.000 |
| Part III | |
| Glycerin 99 Percent, USP | 2.000 |
| Part IV | |
| Syloid B-30 (Silica Gel HSG-750) | 13.000 |
| Sicosil 63M | 4.000 |
| Titanium Dioxide ANSB Div Sun | 1.000 |
| Sodium Lauryl Sulfate, NF | 2.400 |
| Part V | |
| Periodontal Toothpaste-Flavor Mix | 1.500 |

*Adjust concentration of SRF to 3000 units/oz. of product.

Part I

Sodium benzoate, sodium saccharin, sodium fluoride, sodium chloride, zinc chloride and SRF were placed in a suitable container and mixed for 5 minutes. Sorbitol solution was added and stirring continued for an additional 5 minutes. To the mixture was added the sodium bicarbonate and the resulting mixture heated to 60° C. with stirring and maintained at that temperature for 10 minutes. The mixture was cooled to 25° C. and deaerated.

Part II

Concurrently the glycerin was placed in a separate suitable container equipped with a stirrer. The carboxymethylcellulose was added with stirring until evenly dispersed. The carboxymethylcellulose dispersion was transferred to the mixture of Part I with the aid of vacuum. To this was added the glycerin of Part III with the aid of rinsing water. The mixture was deaerated and mixed 30 minutes. The viscosity and pH was checked. To this mixture was added a blended mixture of the Syloid, Sicosil, titanium dioxide and sodium lauryl sulfate. The resulting mixture was deareated.

To the deareated mixture was added the flavor mix of Part V with the aid of rinsing water. The resulting mixture was stirred for an additional 20 minutes and packaged in toothpaste tubes.

The flavor component contains the same ingredients and is produced by the same method as in Example 1.

EXAMPLE 4

Another embodiment of the periodontal toothpaste of the invention is described below.

| Phase | Ingredient | % By Weight |
|---|---|---|
| A | Glycerine 96% | 5.00 |
| A | CMC 7MF | 1.00 |
| B | Sorbitol 70% | 15.00 |
| C | Deionized Water | 22.61 |
| C | Zinc Chloride | 0.25 |
| C | Sodium Benzoate | 0.10 |
| C | Sodium Saccharine | 0.25 |
| C | Sodium Fluoride | 0.22 |
| C | Sodium Chloride | 5.00 |
| C | SRF | 1.37 |
| C | Sodium Bicarbonate | 20.00 |
| D | Syloid B-30 | 13.00 |
| D | Sicosil 63M | 4.00 |
| E | Titanium Dioxide #3328 | 1.00 |
| E | Sorbitol 70% | 2.00 |
| F | Sorbitol 70% | 5.00 |
| F | Sodium Lauryl Sulfate | 2.40 |
| F | Flavor | 1.50 |
| G | D & C Red #33 (1%) | 0.30 |

The components are formulated into a toothpaste by the procedure of Example 1.

The flavor component present to the extent of 0.30% by weight contains the ingredients and is produced by the procedure of Example 1.

The method in accordance with this invention, to treat gingivitis or to induce an anti-gingivitis effect, comprises administering to the oral cavity of an animal organism, preferably humans, suffering from gingivitis, an amount sufficient to retard and treat said gingivitis.

The preferred method is by brushing the toothpaste formulation onto the teeth and gums, and rinsing out. The procedure is used three times per day until results conform to the dentist's treatment desires.

In general, the pharmaceutical preparation of the present invention attacks gram-negative and gram-positive bacteria, both the aerobic and anaerobic spirochetes, large virus and certain protozoa, in addition to exercising an antifungal activity for oral infections caused by *Candida albicans*. It acts as a protective for irritated and inflamed mucous membranes and as an oral lavage, and assists in the removal of tenacious mucus.

The antimicrobial activity of the toothpaste of Example 3 was determined against various organisms in an agar diffusion assay according to the following procedure:

1. A 24 hour culture of each organism was diluted 1-1000 in sterile saline (1-100 for C. albicans).
2. 0.1 ml of this dilution was streaked onto the surface of 3 trypticase soy agar plates.
3. One 8 mm well was dug into each plate with a cork borer.
4. Each well was filled with the toothpaste.
5. The plates were incubated for 24 hours at 35C and then the zones of inhibition were measured in mm. The results are in Table 1.

TABLE 1

Zone of Inhibition against various organisms for Toothpaste of Example 3 (in millimeters)

| Organism | Well #1 | Well #2 | Well #3 | Average |
|---|---|---|---|---|
| C. albicans | 50 | 50 | 47 | 49 |

TABLE 1-continued

Zone of Inhibition against various organisms for Toothpaste of Example 3 (in millimeters)

| Organism | Well #1 | Well #2 | Well #3 | Average |
|---|---|---|---|---|
| Strep. mutans | 42 | 44 | 44 | 43.3 |
| Ps. aeruginosa | 23 | 21 | 20 | 21.3 |

EXAMPLE 5

| | Grams |
|---|---|
| Gelatin (finely powdered) | 47 |
| SRF | 3000 units per oz. of product |
| Mineral oil | 47.5 |
| Polyethylene (mol. wt. 21,000) | 2.5 |

As a night time adjunct to the above brushing treatment of gingivitis the active ingredient, SRF, may be formulated in a vehicle suitable for topical application to the gingavae. Said formulation is a viscous pharmaceutical composition essentially comprising SRF and an intimate admixture of particulate gelatin with mineral oil containing dispersed therein polyethylene having a molecular weight of at least 3,500 in an amount equal to approximately 0.25% to 50% of the combined weight of polyethylene and mineral oil, the SRF preferably representing about 3000 units per oz. of the composition.

(a) A polyethylene-mineral oil dispersion is prepared as described in U.S. Pat. No. 2,628,187.

(b) The SRF is blended with an equal weight of the dispersion of (a) in a planetary type mixer and then the material is passed through a roller mill. To 2 gm. of milled material is added 2 gm. of the dispersion (a) with mixing in a planetary type mixer until homogeneous. Again add (a) in an amount equal to that in the planetary mixer and mix until homogeneous. Continue this geometric addition process until the dispersion (a) has been completely utilized.

(c) The gelatin is introduced into the bowl of a planetary type mixer, covered with (b) and blended until homogeneous.

It is thus seen that I have provided a dentifrice which is eminently satisfactory to accomplish all of the aforesaid stated objectives.

I claim:

1. A pharmaceutical composition comprising skin respiratory factor (SRF), sodium chloride, and bicarbonate, fluoride, and zinc ions in a suitable toothpaste vehicle, wherein the range of SRF present is from 2700 to 3300 units per oz., total fluoride is present in the range 900 to 1100 ppm, bicarbonate ion is present in the range 13.05 to 20.00% by weight, sodium chloride is present in the range 4.50 to 10.5% by weight and zinc ion is present in the range 0.108 to 0.132% by weight.

2. A pharmaceutical composition according to claim 1 wherein the zinc ion is in the form of a salt selected from the group consisting of zinc chloride, zinc citrate, zinc acetate, zinc lactate, and zinc salicylate.

3. A pharmaceutical composition according to claim 1 comprising about 1.23% by weight SRF, 10% by weight sodium chloride, 15% by weight sodium bicarbonate, 0.22% by weight sodium fluoride, 0.25% by weight zinc chloride in a suitable toothpaste vehicle.

4. Method of treating gingivitis by administering to the oral cavity of a human suffering from gingivitis, a pharmaceutical composition in accordance with claim 1 comprising skin respiratory factor (SRF), sodium chloride, and bicarbonate, fluoride and zinc ions in a suitable toothpaste vehicle.

* * * * *